US008592159B2

(12) United States Patent
Nagasawa et al.

(10) Patent No.: US 8,592,159 B2
(45) Date of Patent: Nov. 26, 2013

(54) METHOD FOR DETECTING PRESUMED IGA NEPHROPATHY AND METHOD FOR SCREENING IGA NEPHROPATHY PATIENTS

(75) Inventors: Yasuyuki Nagasawa, Osaka (JP); Kenichiro Iio, Osaka (JP); Yoshitaka Isaka, Osaka (JP); Shinji Fukuda, Kanagawa (JP); Hiroshi Ohno, Kanagawa (JP)

(73) Assignee: Osaka University, Osaka (JP)

( * ) Notice: Subject to any disclaimer, the term of this patent is extended or adjusted under 35 U.S.C. 154(b) by 11 days.

(21) Appl. No.: 13/148,344

(22) PCT Filed: Feb. 10, 2010

(86) PCT No.: PCT/JP2010/051909
§ 371 (c)(1),
(2), (4) Date: Sep. 30, 2011

(87) PCT Pub. No.: WO2010/092961
PCT Pub. Date: Aug. 19, 2010

(65) Prior Publication Data
US 2012/0034611 A1  Feb. 9, 2012

(30) Foreign Application Priority Data
Feb. 12, 2009 (JP) .................................. 2009-029227

(51) Int. Cl.
*C12Q 1/68* (2006.01)
*C07H 21/04* (2006.01)
*C07H 21/02* (2006.01)

(52) U.S. Cl.
USPC ............................... 435/6.12; 536/23; 536/24

(58) Field of Classification Search
None
See application file for complete search history.

(56) References Cited

U.S. PATENT DOCUMENTS
2006/0188523 A1* 8/2006 Pei et al. .................... 424/234.1

FOREIGN PATENT DOCUMENTS
JP  2002-296276  10/2002

OTHER PUBLICATIONS

Matsutani et al. (Bacterial florae of palatine tonsils in patients with IgA nephropathy, International Congress Series 1257 (2003) 235-237.*
Nozawa et al. (Investigation of The Bacterial Flora in Tonsil from Patients with Focal Tonsillar Infection, Journal of Japan Society for Infectious Diseases in Otolaryngology, (Jan. 5, 2004), vol. 22, No. 1, pp. 139 to 146).*
Liu (Introductory Remarks, in Molecular Detection of Human Bacterial Pathogens, 2011, pp. 1-10.*
Xie et al. (Relationship between tonsils and IgA nephropathy as well as indications of tonsillectomy, Kidney International, vol. 65 (2004), pp. 1135-1144).*
Komatsu et al. (Effect of Tonsillectomy Plus Steroid Pulse Therapy on Clinical Remission of IgA Nephropathy: A Controlled Study, Clin J Am Soc Nephrol. Sep. 2008; 3(5): 1301-1307).*
Wang et al. (Colony Multiplex PCR Assay for Identification and Differentiation of Campylobacter jejuni, C. coli, C. lari, C. upsaliensis, and C. fetus subsp. fetus, Journal of Clinical Microbiology, Dec. 2002, p. 4744-4747).*
Carter et al. (IgA Nephropathy Associated with Campylobacter jejuni Enteritis, Nephron, 1991, 58:101-102).*
Extended European Search Report issued Oct. 8, 2012 in corresponding European Application No. 10741238.9.
Asai, Yasuyuki, et al., "Detection and Quantification of Oral Treponemes in Subgingival Plaque by Real-Time PCR", Journal of Clinical Microbiology, vol. 40, No. 9, Sep. 2002, pp. 3334-3340.
Kawasaki, Susumu, et al., "Species-Specific Identification of Campylobacters by PCR-Restriction Fragment Length Polymorphism and PCR Targeting of the Gyrase B Gene", Applied and Environmental Microbiology, vol. 74, No. 8, Feb. 2008, pp. 2529-2533.
Hayashi, Fumiko, et al., "Subgingival distribution of *Campylobacter rectus* and *Tannerella forsythensis* in healthy children with primary dentition", Archives of Oral Biology, vol. 51, No. 1, Jan. 2006, pp. 10-14.
Xie, Yuansheng, et al., "Relationship between tonsils and IgA nephropathy as well as indications of tonsillectomy", Kidney International, vol. 65, No. 4, Apr. 2004, pp. 1135-1144.
Iio, Kenichiro, et al., "Microarray analysis of tonsils in immunoglobulin A nephropathy patients", Biochemical and Biophysical Research Communications, vol. 393, No. 4, Mar. 2010, pp. 565-570.
H. Nozawa et al., "Investigation of the Bacterial Flora in Tonsil from Patients with Focal Tonsillar Infection", Journal of Japan Society for Infectious Diseases in Otolaryngology, vol. 22, No. 1, pp. 139-146, May 1, 2004 (with partial English translation).
H. Akagi et al., "Tokushu•Hento Tekishutsu Shujutsu no Tekio up date IgA Jinsho to Henteki", Monthly Book ENTONI, No. 39, pp. 21-26, Jul. 2004 (with partial English translation).
Y. Nagasawa et al., "Iga Jinsho Kanja Hento ni Tokuiteki na Saikinso no Morateki Kento", Japanese Journal of Nephrology, vol. 51, No. 3, p. 284, Apr. 2009 (with English translation).

(Continued)

*Primary Examiner* — Christopher M Babic
*Assistant Examiner* — Aaron Priest
(74) *Attorney, Agent, or Firm* — Wenderoth, Lind & Ponack, L.L.P.

(57) ABSTRACT

A process for detecting presumed IgA nephropathy by detection of *Treponema* bacteria and/or *Campylobacter* bacteria present in a sample from the tonsil of a subject who, optionally, has a positive result in a urinary protein test and/or a urinary occult blood test, or whom is diagnosed with possible IgA nephropathy. Also, a process for detecting an IgA nephropathy patient for whom tonsillectomy is effective by detecting *Treponema* bacteria or Campylobacter bacteria.

18 Claims, 5 Drawing Sheets

(56) References Cited

OTHER PUBLICATIONS

M. Tokuda et al., "Direct Evidence of the Production of IgA by Tonsillar Lymphocytes and the Binding of IgA to the Glomerular Mesangium of IgA Nephropathy Patients", Acta Otolaryngol, Suppl. vol. 523, pp. 182-184, 1996.

H. Akagi et al., "Prognosis of Tonsillectomy in Patients with IgA Nephropathy", Acta Otolaryngol, Suppl. 540, pp. 64-66, 1999.

O. Hotta et al., "Tonsillectomy and Steroid Pulse Therapy Significantly Impact on Clinical Remission in Patients with IgA Nephropathy", American Journal of Kidney Diseases, vol. 38, No. 4, pp. 736-743, Oct. 2001.

S. Suzuki et al., "Haemophilus Parainfluenzae Antigen and Antibody in Renal Biopsy Samples and Serum of Patients with IgA Nephropathy", The Lancet, vol. 343, pp. 12-20, Jan. 1, 1994.

E. Maeda et al., "Mansei Hentouen to IgA Jinshou Shourei no Hyousou narabini Shinbu ni okeru Hentousaikinsou no Hikakukentou", 109th Annual Meeting of ORL Society of Japan, Apr. 20, 2008 (with English translation).

A. Horii et al., "IgA Jinsho ni okeru Henteki Suteroidoparusu Ryouhou no Yogoyosoku Inshi ni tsuite", 109th Annual Meeting of ORL Society of Japan, Apr. 20, 2008 (with English translation).

S. Suzuki et al., "IgA Jinsho no Hasshou ni okeru Hemophilusu parainfluenzae kin no kanyo ni kansuru Kenkyuu", Tokutei Shikkan no Biseibutsugakuteki Gennin Kenkyuu ni kansuru Kenkyuu, 2002 (with English Abstract).

English translation of International Preliminary Report on Patentability dated Sep. 13, 2011.

\* cited by examiner

METHOD FOR DETECTING PRESUMED IGA NEPHROPATHY AND METHOD FOR SCREENING IGA NEPHROPATHY PATIENTS This application is a U.S. national stage of International Application No. PCT/W2010/051909 filed Feb. 10, 2010.

TECHNICAL FIELD

The present invention relates to a method for detecting presumed IgA nephropathy and a method for screening IgA nephropathy patients. In particular, the present invention relates to a method for detecting presumed IgA nephropathy with a high accuracy before definitive diagnosis of IgA nephropathy, and a method for screening for an IgA nephropathy patient for whom tonsillectomy is effective.

BACKGROUND ART

IgA nephropathy is a type of chronic glomerulonephritis characterized by IgA deposition dominantly in the glomerular mesangium area of the kidney. IgA nephropathy cases account for the majority of chronic glomerulonephritis cases in Japan, and as a single renal disease, are largest in number. Of such IgA nephropathy cases, 15 to 30% having a poor prognosis progress into renal failure, and there is no radical therapy because the etiology of IgA nephropathy is still unknown. The definitive diagnosis of IgA nephropathy is a heavy burden on patients because it is based on a method involving biopsy in which a portion of the kidney is excised and immunologically stained to confirm IgA immune complex deposition in the mesangium. Accordingly, desired is a method for detecting presumed IgA nephropathy with a high accuracy, the method being simply and quickly practicable without physical burden on subjects before renal biopsy.

It is known that, regarding IgA, which is categorized into two types IgA1 and IgA2, IgA1 is produced in the upper gastrointestinal tract, the respiratory tract and the tonsil while IgA2 is produced in the lower gastrointestinal tract. Since IgA nephropathy is associated with IgA1 deposition in the kidney, tonsillectomy as a therapy for IgA nephropathy patients has been performed in recent years.

Non Patent Literature 1 reports that three years after tonsillectomy was performed in 16 IgA nephropathy patients, remission of proteinuria was observed in 56.3% of them. Non Patent Literature 2 also reports that tonsillectomy was performed in 24 IgA nephropathy patients and that remission of proteinuria was observed in 41.7% of them six months later and in 50% of them two years later. Further, Non Patent Literature 3 reports that combination of tonsillectomy and steroid pulse therapy produced remission of both of proteinuria and hematuria in about 60% of IgA nephropathy patients.

However, tonsillectomy is not effective for about 40% of IgA nephropathy patients, and whether or not tonsillectomy is effective for each individual patient cannot be presumed beforehand. Since tonsillectomy operation requires general anesthesia and thus is heavy physical burden on the patients, desired is the establishment of a method for screening for, with a high accuracy, a patient for whom tonsillectomy is effective.

CITATION LIST

Non Patent Literature

Non Patent Literature 1:
Tokuda M et al. Acta Otolaryngol Suppl 523; 182-184, 1988.

Non Patent Literature 2:
Akagi H et al. Acta Otolaryngol Suppl 540; 64-66, 1999.
Non Patent Literature 3:
Hotta et al. Am J Kid Dis 38, 736-743, 2001.

SUMMARY OF INVENTION

Technical Problem

An object of the present invention is to provide a method for detecting presumed IgA nephropathy with a high accuracy, the method being simply and quickly practicable without physical burden on subjects. Another object of the present invention is to provide a method for screening for, with a high accuracy, an IgA nephropathy patient for whom tonsillectomy is effective in therapy of IgA nephropathy.

Solution to Problem

The present invention includes the following, in order to solve the above-mentioned problems.
[1] A method for detecting presumed IgA nephropathy, comprising the step of detecting *Treponema* bacteria or *Campylobacter* bacteria present in a sample derived from the tonsil of a subject.
[2] The method according to the above [1], wherein the step involves detecting a nucleic acid specific to *Treponema* bacteria or *Campylobacter* bacteria.
[3] The method according to the above [1], wherein the step involves using an antibody capable of specifically binding to *Treponema* bacteria or *Campylobacter* bacteria.
[4] The method according to the above [1], wherein the *Treponema* bacteria are one or more kinds selected from bacteria detectable by PCR using, as a template, cDNA obtained by reverse transcription from total RNA extracted from *Treponema* bacteria, and using a primer set of a primer consisting of the base sequence represented by SEQ ID NO: 1 and a primer consisting of the base sequence represented by SEQ ID NO: 2.
[5] The method according to the above [1], wherein the *Treponema* bacteria are one or more kinds selected from the group consisting of *Treponema denticola, Treponema vincentii, Treponema medium, Treponema socranskii, Treponema phagedenis, Treponema pectinovorum, Treponema amylovorum, Treponema maltophilum, Treponema bryantii, Treponema pallidum, Treponema saccharophilum* and *Treponema succinifaciens*.
[6] The method according to the above [1], wherein the *Campylobacter* bacteria are one or more kinds selected from the group consisting of *Campylobacter rectus, Campylobacter jejuni, Campylobacter coli, Campylobacter concisus, Campylobacter curvus, Campylobacter showae, Campylobacter mucosalis, Campylobacter fetus, Campylobacter hyointestinalis, Campylobacter sputorum, Campylobacter helveticus, Campylobacter upsaliensis* and *Campylobacter lari*.
[7] The method according to any one of the above [1] to [6], wherein the subject has a positive result on at least one of a urinary protein test and a urinary occult blood test.
[8] A kit for detecting presumed IgA nephropathy, comprising at least one of the following (a) to (d):
(a) a primer set for specific detection of *Treponema* bacteria,
(b) a primer set for specific detection of *Campylobacter* bacteria,
(c) an antibody capable of specifically binding to *Treponema* bacteria, and (d) an antibody capable of specifically binding to *Campylobacter* bacteria.

[9] A method for screening for an IgA nephropathy patient for whom tonsillectomy is effective in therapy of IgA nephropathy, the method comprising the step of detecting *Treponema* bacteria or *Campylobacter* bacteria present in a sample derived from the tonsil of an IgA nephropathy patient.

[10] A method for screening for an IgA nephropathy patient for whom tonsillectomy plus steroid pulse therapy is effective in therapy of IgA nephropathy, the method comprising the step of detecting *Treponema* bacteria or *Campylobacter* bacteria present in a sample derived from the tonsil of an IgA nephropathy patient.

[11] The method according to the above [9] or [10], wherein the step involves detecting a nucleic acid specific to *Treponema* bacteria or *Campylobacter* bacteria.

[12] The method according to the above [9] or [10], wherein the step involves using an antibody capable of specifically binding to *Treponema* bacteria or *Campylobacter* bacteria.

[13] The method according to the above [9] or [10], wherein the *Treponema* bacteria are one or more kinds selected from bacteria detectable by PCR using, as a template, cDNA obtained by reverse transcription from total RNA extracted from *Treponema* bacteria, and using a primer set of a primer consisting of the base sequence represented by SEQ ID NO: 1 and a primer consisting of the base sequence represented by SEQ ID NO: 2.

[14] The method according to the above [9] or [10], wherein the *Treponema* bacteria are one or more kinds selected from the group consisting of *Treponema denticola, Treponema vincentii, Treponema medium, Treponema socranskii, Treponema phagedenis, Treponema pectinovorum, Treponema amylovorum, Treponema maltophilum, Treponema bryantii, Treponema pallidum, Treponema saccharophilum* and *Treponema succinifaciens*.

[15] The method according to the above [9] or [10], wherein the *Campylobacter* bacteria are one or more kinds selected from the group consisting of *Campylobacter rectus, Campylobacter jejuni, Campylobacter coli, Campylobacter concisus, Campylobacter curvus, Campylobacter showae, Campylobacter mucosalis, Campylobacter fetus, Campylobacter hyointestinalis, Campylobacter sputorum, Campylobacter helveticus, Campylobacter upsaliensis* and *Campylobacter lari*.

[16] A kit for screening for an IgA nephropathy patient for whom tonsillectomy is effective in therapy of IgA nephropathy, the kit comprising at least one of the following (a) to (d):
(a) a primer set for specific detection of *Treponema* bacteria,
(b) a primer set for specific detection of *Campylobacter* bacteria,
(c) an antibody capable of specifically binding to *Treponema* bacteria, and
(d) an antibody capable of specifically binding to *Campylobacter* bacteria.

According to the present invention, whether or not a subject is affected by IgA nephropathy can be presumed with a high accuracy, in a simple and quick manner without physical burden on the subject. According to the present invention, an IgA nephropathy patient for whom tonsillectomy is effective in therapy of IgA nephropathy can be selected with a high accuracy, in a simple and quick manner without physical burden on the patient.

DESCRIPTION OF EMBODIMENTS

Figure 1:
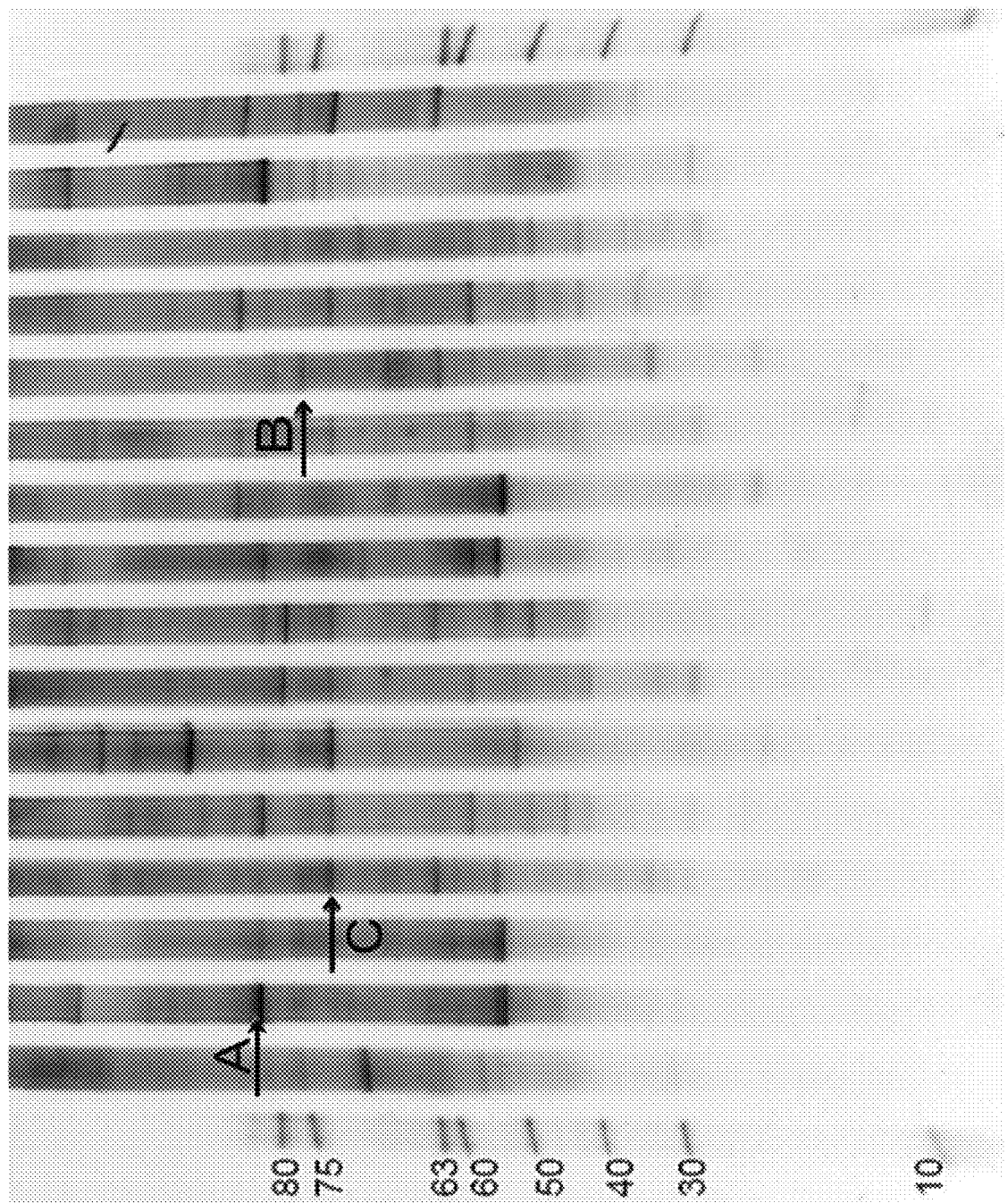
FIG. 1 is an electrophoretic pattern resulting from DGGE performed for comprehensive analysis of tonsil bacterial flora.

The present inventors comprehensively analyzed bacterial flora in the tonsils excised from patients with renal biopsy-proven IgA nephropathy and from patients with chronic tonsillitis. As a result, they found that bacterial flora in the tonsil is different between IgA nephropathy patients and chronic tonsillitis patients, and that *Treponema* bacteria, *Haemophilus* bacteria and *Campylobacter* bacteria are present with a high probability in IgA nephropathy patients. These findings indicate that the presence of *Treponema* bacteria, *Haemophilus* bacteria or *Campylobacter* bacteria in the tonsil is a highly probable sign of IgA nephropathy. Although *Haemophilus* bacteria had been suggested to be associated with IgA nephropathy before this patent application, it was first found by the present inventors that the positive rates for *Treponema* bacteria and *Campylobacter* bacteria are high in the tonsils of IgA nephropathy patients.

Further, the present inventors found that it is greatly effective to provide tonsillectomy therapy to IgA nephropathy patients who are positive in detection of *Treponema* bacteria or *Campylobacter* bacteria in the tonsil, and finally completed the present invention.

That is, the present invention relates to a method for detecting presumed IgA nephropathy, the method comprising the step of detecting *Treponema* bacteria or *Campylobacter* bacteria in a sample derived from the tonsil of a subject. The present invention also relates to a method for screening for an IgA nephropathy patient for whom tonsillectomy is effective or tonsillectomy plus steroid pulse therapy is effective in therapy of IgA nephropathy, the method comprising the step of detecting *Treponema* bacteria or *Campylobacter* bacteria in a sample derived from the tonsil of an IgA nephropathy patient.

In the method of the present invention for detecting presumed IgA nephropathy, the subject is not particularly limited, but preferred is one suspected to have developed IgA nephropathy. Examples of the one suspected to have developed IgA nephropathy include those who have a positive result on at least one of a urinary protein test and a urinary occult blood test. More specifically, included are those who have positive results for proteinuria and hematuria in a urine test performed as medical checkup at schools, companies and the like, or as outpatient care etc., and continue to have such abnormal results in further urine tests. IgA nephropathy is often accompanied by both of proteinuria and hematuria, but in some cases by only hematuria, and thus the subject is preferably one who continues to be positive for at least one of proteinuria and hematuria. Urinary protein positive (proteinuria) and urinary occult blood positive (hematuria) can be determined by use of a known urinalysis test paper generally used for urinalysis, for example.

Conventionally, a subject suspected to have developed IgA nephropathy cannot be diagnosed without renal biopsy or histological analysis. This means that a subject who ends up being diagnosed as not having IgA nephropathy also undergoes unnecessary physical burden. By use of the method of the present invention for detecting presumed IgA nephropathy, renal biopsy can be limited to subjects who have IgA nephropathy with a high probability, and therefore, unnecessary physical burden can be avoided.

In the method of the present invention for screening IgA nephropathy patients, the IgA nephropathy patient to be screened is not particularly limited, but preferred is an IgA nephropathy patient who has not undergone tonsillectomy before.

Conventionally, tonsillectomy is not effective for about 40% of IgA nephropathy patients. By use of the method of the present invention for screening IgA nephropathy patients, tonsillectomy can be provided only to a patient for whom tonsillectomy is effective with a high probability, and therefore, unnecessary physical burden and economic burden can be avoided.

Hereinafter, the method for detecting presumed IgA nephropathy and the method for screening IgA nephropathy patients are collectively referred to as "the method of the present invention", and the contents common in both will be described in detail.

In the method of the present invention, *Treponema* bacteria targeted for detection are not particularly limited, and all the *Treponema* bacteria that may be present in the tonsil are included. Examples of the *Treponema* bacteria include bacteria detectable by PCR, for example, using, as a template, cDNA obtained by reverse transcription from total RNA extracted from *Treponema* bacteria and using a primer set of the forward primer (TTACGTGCCAGCAGCCGCGG-TAAC, SEQ ID NO: 1) and the reverse primer (GTCRYMG-GCAGTTCCGCCWGAGTC, SEQ ID NO: 2). Here, as a base symbol, R represents guanine (G) or adenine (A), Y represents thymine (T) or cytosine (C), M represents adenine (A) or cytosine (C), and W represents adenine (A) or thymine (T).

Specific examples of the *Treponema* bacteria include *Treponema denticola*, *Treponema vincentii*, *Treponema medium*, *Treponema socranskii*, *Treponema phagedenis*, *Treponema pectinovorum*, *Treponema amylovorum*, *Treponema maltophilum*, *Treponema bryantii*, *Treponema pallidum*, *Treponema saccharophilum* and *Treponema succinifaciens*.

In the method of the present invention, Campylobacter bacteria targeted for detection are not particularly limited, and all the *Campylobacter* bacteria that may be present in the tonsil are included. Examples of the *Campylobacter* bacteria include *Campylobacter rectus*, *Campylobacter jejuni*, *Campylobacter coli*, *Campylobacter concisus*, *Campylobacter curvus*, *Campylobacter showae*, *Campylobacter mucosalis*, *Campylobacter fetus*, *Campylobacter hyointestinalis*, *Campylobacter sputorum*, *Campylobacter helveticus*, *Campylobacter upsaliensis* and *Campylobacter lari*. Inter alia, preferred is *Campylobacter rectus*.

The sample to be used in the method of the present invention is not particularly limited as long as it is derived from the tonsil of a subject or a patient. Examples of the sample include DNA, RNA, cell suspension and cell lysate each of which is prepared from tonsil tissue, tonsil swab, etc. All these samples can be prepared according to a method well-known to those skilled in the art.

The method for detecting *Treponema* bacteria or *Campylobacter* bacteria is not particularly limited as long as it can achieve specific detection of *Treponema* bacteria or *Campylobacter* bacteria. Examples thereof include a method intended for detection of a nucleic acid specific to *Treponema* bacteria or *Campylobacter* bacteria, and a method using an antibody capable of specifically binding to *Treponema* bacteria or *Campylobacter* bacteria.

In the method intended for detection of a nucleic acid, the nucleic acid may be DNA or RNA. A known detection method for nucleic acids is preferably used for the present invention. Specific examples thereof include PCR, Southern blot, Northern blot, RT-PCR, in situ hybridization, in situ PCR and DNA array assay. Inter alia, preferred is RT-PCR in view of detectability, operation simplicity, quick results and low cost. In the case where RT-PCR is used for detection of *Treponema* bacteria or *Campylobacter* bacteria, total RNA prepared from tonsil tissue, tonsil swab, etc. is used as the sample. The total RNA can be prepared according to a known method.

RT-PCR can be performed according to a method well-known to those skilled in the art. For example, cDNA is prepared by use of reverse transcriptase from total RNA prepared from tonsil tissue, tonsil swab, etc., and then PCR is performed using the obtained cDNA as a template and using a primer set for specific amplification of a DNA fragment derived from bacteria targeted for detection. The primer set for specific amplification of a DNA fragment derived from bacteria targeted for detection is not particularly limited, and primers can be designed according to a known method based on the data available in known databases (for example, Gen-Bank etc.), including the genome sequence and the ribosomal RNA sequence of the bacteria targeted for detection. Examples of the primer set that can be preferably used for the method of the present invention include, but are not limited to, the following sets.

An example of the primer set for specific detection of *Treponema* bacteria is as follows.

```
Forward primer:
TTACGTGCCAGCAGCCGCGGTAAC      (SEQ ID NO: 1)

Reverse primer:
GTCRYMGGCAGTTCCGCCWGAGTC      (SEQ ID NO: 2)
```

A 657 bp DNA fragment is supposed to be amplified by use of this primer set (J Clin Microbiol, 2002. 40(9): 3334-40.).

An example of the primer set for specific detection of *Treponema denticola* is as follows.

```
Forward primer:
TAATACCGAATGTGCTCATTTACAT     (SEQ ID NO: 3)

Reverse primer:
CTGCCATATCTCTATGTCATTGCTCTT   (SEQ ID NO: 4)
```

An 860 bp DNA fragment is supposed to be amplified by use of this primer set (J Clin Microbiol, 2002. 40(9): 3334-40.).

An example of the primer set for specific detection of *Treponema vincentii* is as follows.

```
Forward primer:
GTCTCAATGGTTCATAAGAA          (SEQ ID NO: 5)

Reverse primer:
CAAGCCTTATCTCTAAGACT          (SEQ ID NO: 6)
```

An 851 bp DNA fragment is supposed to be amplified by use of this primer set (J Clin Microbial, 2002. 40(9): 3334-40.).

An example of the primer set for specific detection of *Treponema medium* is as follows.

```
Forward primer:
CACTCAGTGCTTCATAAGGG        (SEQ ID NO: 7)

Reverse primer:
CCGGCCTTATCTCTAAGACC        (SEQ ID NO: 8)
```

An 851 bp DNA fragment is supposed to be amplified by use of this primer set (J Clin Microbiol, 2002. 40(9): 3334-40.).

An example of the primer set for specific detection of *Campylobacter rectus* is as follows.

```
Forward primer:
TTTCGGAGCGTAAACTCCTTTTC     (SEQ ID NO: 9)

Reverse primer:
TTTCTGCAAGCAGACACTCTT       (SEQ ID NO: 10)
```

A 598 bp DNA fragment is supposed to be amplified by use of this primer set (Archives of Oral Biology, 2006. 51: 10-14.).

An example of the primer set for specific detection of *Campylobacter jejuni* is as follows.

```
Forward primer:
AGAATGGGTTTAACTCGTGTGATAAGT (SEQ ID NO: 11)

Reverse primer:
TACCACGCAAAGGCAGTATAGCT     (SEQ ID NO: 12)
```

A 493 bp DNA fragment is supposed to be amplified by use of this primer set (Appl Environ Microbiol, 2008. 74(8): 2529-33.).

An example of the primer set for specific detection of *Campylobacter coli* is as follows.

```
Forward primer:
AAATGCTAGTGCTAGGGAAAAAGACTCT (SEQ ID NO: 13)

Reverse primer:
TGAGGTTCAGGCACTTTTACACTTACTAC (SEQ ID NO: 14)
```

A 96 bp DNA fragment is supposed to be amplified by use of this primer set (Appl Environ Microbiol, 2008. 74(8): 2529-33.).

An example of the primer set for specific detection of *Campylobacter concisus* is as follows.

```
Forward primer:
AGCGGGCCTAACAAGAGTTATTACA   (SEQ ID NO: 15)

Reverse primer:
TGTAAGCACGTCAAAAACCATCTTT   (SEQ ID NO: 16)
```

A 217 bp DNA fragment is supposed to be amplified by use of this primer set (Appl Environ Microbiol, 2008. 74(8): 2529-33.).

An example of the primer set for specific detection of *Campylobacter curvus* is as follows.

```
Forward primer:
CTGCCAAAGTAAGGACGCAAGTATA   (SEQ ID NO: 17)

Reverse primer:
GGCAAGATCGCCTGAAATACG       (SEQ ID NO: 18)
```

A 108 bp DNA fragment is supposed to be amplified by use of this primer set (Appl Environ Microbiol, 2008. 74(8): 2529-33.).

An example of the primer set for specific detection of *Campylobacter showae* is as follows.

```
Forward primer:
AGGGTTTAAGCATAGGAACGCTG     (SEQ ID NO: 19)

Reverse primer:
CACCAGATAAAGCTCGCTGATCG     (SEQ ID NO: 20)
```

An 86 bp DNA fragment is supposed to be amplified by use of this primer set (Appl Environ Microbiol, 2008. 74(8): 2529-33.).

An example of the primer set for specific detection of *Campylobacter mucosalis* is as follows.

```
Forward primer:
TGCGATTATGAACAAGGCCCTA      (SEQ ID NO: 21)

Reverse primer:
TCGCTTGAAACACACGGTCA        (SEQ ID NO: 22)
```

A 224 bp DNA fragment is supposed to be amplified by use of this primer set (Appl Environ Microbiol, 2008. 74(8): 2529-33.).

An example of the primer set for specific detection of *Campylobacter fetus* is as follows.

```
Forward primer:
AGAGCTGGGCTTACAAGAGCTATTACA (SEQ ID NO: 23)

Reverse primer:
GGTAAAATCGCTTGAAACGCTCTAT   (SEQ ID NO: 24)
```

A 482 bp DNA fragment is supposed to be amplified by use of this primer set (Appl Environ Microbiol, 2008. 74(8): 2529-33.).

An example of the primer set for specific detection of *Campylobacter hyointestinalis* is as follows.

```
Forward primer:
CGGTCAAAAGATGACTTTTGAAGTACTT (SEQ ID NO: 25)

Reverse primer:
GCTTCCCTGCCACGAGCT          (SEQ ID NO: 26)
```

A 108 bp DNA fragment is supposed to be amplified by use of this primer set (Appl Environ Microbiol, 2008. 74(8): 2529-33.).

An example of the primer set for specific detection of *Campylobacter sputorum* is as follows.

```
Forward primer:
AGCTTTACTTGCTGCAAGAGGAAGA   (SEQ ID NO: 27)

Reverse primer:
AGGAAGCGTTCCAACAGAAAAGTT    (SEQ ID NO: 28)
```

A 94 bp DNA fragment is supposed to be amplified by use of this primer set (Appl Environ Microbiol, 2008. 74(8): 2529-33.).

An example of the primer set for specific detection of *Campylobacter helveticus* is as follows.

```
Forward primer:
CAATAACATACGCACACCAGATGGA      (SEQ ID NO: 29)

Reverse primer:
CAGGCACTTTAACGCTCACTATGG       (SEQ ID NO: 30)
```

A 176 bp DNA fragment is supposed to be amplified by use of this primer set (Appl Environ Microbiol, 2008. 74(8): 2529-33.).

An example of the primer set for specific detection of *Campylobacter upsaliensis* is as follows.

```
Forward primer:
GCTTACGCGTGTAATTACAAACTATGTC   (SEQ ID NO: 31)

Reverse primer:
AATTGCCTTAGCCTCGATAGGG         (SEQ ID NO: 32)
```

A 250 bp DNA fragment is supposed to be amplified by use of this primer set (Appl Environ Microbiol, 2008. 74(8): 2529-33.).

An example of the primer set for specific detection of *Campylobacter lari* is as follows.

```
Forward primer:
CTATGTTCGTCCTATAGTTTCTAAGGCTTC (SEQ ID NO: 33)

Reverse primer:
CCAGCACTATCACCCTCAACTAAATAA    (SEQ ID NO: 34)
```

A 250 bp DNA fragment is supposed to be amplified by use of this primer set (Appl. Environ Microbiol, 2008. 74(8): 2529-33.).

In the method using an antibody capable of specifically binding to *Treponema* bacteria or *Campylobacter* bacteria, the antibody is, for detection of *Treponema* bacteria, an antibody that binds specifically to *Treponema* bacteria, and, for detection of *Campylobacter* bacteria, an antibody that binds specifically to *Campylobacter* bacteria. The antibody may be a polyclonal or monoclonal antibody. The antibody also may be a complete antibody molecule or an antibody fragment with specific binding ability (for example, a Fab fragment, F(ab')$_2$ fragment, etc.). The antibody that binds specifically to *Treponema* bacteria (a polyclonal antibody, a monoclonal antibody or an antibody fragment) and the antibody that binds specifically to *Campylobacter* bacteria (a polyclonal antibody, a monoclonal antibody and an antibody fragment) can be prepared by use of components of bacteria targeted for detection as an immunogen according to a known method.

Examples of the method using an antibody capable of specifically binding to *Treponema* bacteria or *Campylobacter* bacteria include enzyme immunoassay (EIA), enzyme-linked immunosorbent assay (ELISA), radioimmunoassay (RIA), western blot, immunoprecipitation, immunohistochemical analysis and antibody array assay. Inter alia, preferred is ELISA in view of detectability, operation simplicity, quick results and low cost. In the case where ELISA is used for detection of *Treponema* bacteria or *Campylobacter* bacteria, cell suspension, cell lysate, etc. prepared from tonsil tissue, tonsil swab, etc. are preferably used as the sample.

ELISA can be performed according to a method well-known to those skilled in the art. For example, firstly, a primary antibody that specifically binds to bacteria targeted for detection is allowed to bind to a solid phase such as a well of a microplate and a plastic tube. Next, to the solid phase, a sample derived from the tonsil (cell suspension, cell lysate, etc.) is added and then the solid phase is washed. Then, an enzyme-labeled secondary antibody is added thereto. An unbound secondary antibody is washed out, a chromogenic substrate is added to the solid phase, and the amount of a resulting chromogenic substance is determined from the absorbance measured with a spectrophotometer.

The method of the present invention can be performed simply and quickly by use of a kit. Therefore, the present invention provides a reagent kit for detecting presumed IgA nephropathy, and a reagent kit for screening for an IgA nephropathy patient for whom tonsillectomy is effective (hereinafter, both of the kits are collectively referred to as "the kit of the present invention").

As an embodiment of the kit of the present invention, provided is an RT-PCR kit comprising at least one primer set selected from a primer set for specific detection of *Treponema* bacteria and a primer set for specific detection of *Campylobacter* bacteria. Except for the primer set, the components of the kit are not particularly limited, but the kit preferably further comprises, for example, a reagent for RNA preparation from a tissue or a cell, a reverse transcriptase, a buffer solution for reverse transcription, a heat-resistant DNA polymerase, a PCR reagent, a PCR tube and a PCR plate.

As another embodiment of the kit of the present invention, provided is an ELISA kit comprising at least one antibody selected from an antibody that specifically binds to *Treponema* bacteria, and an antibody that specifically binds to *Campylobacter* bacteria. Except for the antibody, the components of the kit are not particularly limited, but the kit preferably further comprises, for example, a labeled secondary antibody, a chromogenic reagent, a wash buffer solution and an ELISA plate.

As a further embodiment of the kit of the present invention, provided are a kit comprising a DNA array, a kit comprising an antibody array, etc.

EXAMPLES

Hereinafter, the present invention will be illustrated in detail by examples, but is not limited thereto.

Example 1

Examination of Bacterial Flora in Tonsil of IgA Nephropathy Patient (1) Patient Enrollment Tonsil samples were obtained by tonsillectomy from 68 patients who had been hospitalized in the Osaka University Hospital and diagnosed with IgA nephropathy based on renal biopsy, and from 28 chronic tonsillitis patients. Each of the patients submitted written informed consent before sample donation. Immediately after tonsillectomy, the tonsil was subjected to RNA extraction using Trizol (Invitrogen) and the obtained RNA was stored. This examination of IgA nephropathy patients' tonsils was performed by permission of the Ethics Committee of the Osaka University Hospital.

(2) Comprehensive Analysis of Tonsil Bacterial Flora by DGGE (Denaturing Gradient Gel Electrophoresis)

Reverse transcription was performed using the RNAs obtained from the tonsils of the IgA nephropathy patients and of the chronic tonsillitis patients. Each of the obtained cDNAs was used as a template, and PCR was performed using a PCR primer set for the V6 and V8 regions of bacterial 16S ribosomal RNA: universal bacterial primers 954f (CGCCCGC-CGCGCCCCGCGCCCGGCCCGCCGC-CCCCGCMCGCACAAGCGGTGGAGCAT GTGG, SEQ ID NO: 35) and 1369r (GCCCGGGAACGTATTCACCG, SEQ ID NO: 36)(Reference: Yu, Z. and M. Morrison, Comparisons of different hypervariable regions of rrs genes for use in fingerprinting of microbial communities by PCR-denaturing gradient gel electrophoresis. Appl Environ Microbiol, 2004.70 (8): 4800-6). The PCR reaction mixture contained 100 ng of DNA, 10 pmol of each primer, 0.16 mM deoxynucleotide triphosphates, 5 μL of 10×Blend Taq buffer (Toyobo) and 1.25 U of Blend Taq polymerase (Toyobo), and the final volume was made up to 50 with distilled water. The PCR conditions areas follows: after the first cycle of initial denaturation at 95° C. for 4 minutes, denaturation at 95° C. for 30 seconds, annealing at 61° C. for 30 seconds, and extension at 72° C. for 1 minute, 10 cycles were performed under the same conditions except for an annealing temperature decreased by 0.5° C./cycle from 61° C. Then, 25 cycles with an extension temperature of 56° C. were performed, and final extension was performed at 72° C. for 2 hours.

The PCR product was subjected to electrophoresis at 82 V at 60° C. for 15 hours with DCode universal mutation detection System (Bio-Rad laboratories). The gel for the electrophoresis was prepared from a 30% acrylamide/bis (29:1) solution (Bio-Rad laboratories Cat_No. 161-0156). As the marker, DGGE Marker II (10 fragments) (NIPPON GENE, CO., LTD. Cat_No. 315-06404) was used. After electrophoresis, the gel was stained with SYBR Green I (Lonza, Rockland, Me., USA). The position and intensity (density) of bands for each sample were determined by use of the gel imaging system GelDoc XR (Bio-Rad laboratories) (Reference: Muyzer, G., et al., Denaturant gradient gel electrophoresis in microbial ecology. Molecular Microbial Ecology Manual, Vol. 3.4.4, 1998: 1-27).

Multivariate analysis (PLS-DA) of data on the position and intensity of the bands showed that bacterial flora in the tonsil is different between IgA nephropathy and chronic tonsillitis. As a result of Loading plot analysis, bands characteristic of IgA nephropathy were observed.

The result of electrophoresis is shown in FIG. 1. In FIG. 1, the stained bands represent bacteria present in the tonsil, and the bands shown by arrows A, B and C are characteristic of IgA nephropathy. These bands were separately excised from the gel and TA cloning was performed. Then, the base sequence was determined according to a conventional method, and homology search was performed using base sequences registered in a known gene database. As a result, it was clear that bands A, B and C have high homology with *Treponema* bacteria, *Haemophilus segnis* and *Campylobacter rectus*, respectively.

Table 1 shows the positive rate for the bacterium corresponding to each of the above-mentioned bands A, B and C in 68 IgA nephropathy patients or 28 chronic tonsillitis patients. The t-test was used for statistical analysis. As clearly shown in Table 1, there is a high probability that *Treponema* bacteria, *Haemophilus* bacteria and *Campylobacter* bacteria are present in the tonsils of IgA nephropathy patients. Regarding *Haemophilus* bacteria, it was previously reported that components of *Haemophilus parainfluenzae* were detected in the glomeruli and sera of IgA nephropathy patients (Suzuki, et al. Lancet 1994) and the relation of *Haemophilus* bacteria with IgA nephropathy was already suggested. However, regarding *Treponema* bacteria and *Campylobacter* bacteria, the present invention first revealed that the positive rate is high in the tonsils of IgA nephropathy patients, and demonstrated that detection of *Treponema* bacteria or *Campylobacter* bacteria in the tonsil is useful for diagnosis of IgA nephropathy.

TABLE 1

|  | IgA nephropathy | Chronic tonsillitis | P value |
|---|---|---|---|
| Bacterium A (*Treponema* sp.) | 16/68 (24%) | 2/28 (7%) | 0.0443 |
| Bacterium B (*Haemophilus* sp.) | 36/68 (53%) | 7/28 (25%) | 0.0107 |
| Bacterium C (*Campylobacter* sp.) | 33/68 (49%) | 4/28 (14%) | 0.0010 |

Example 2

Detection of *Treponema* Bacteria in Excised Tonsil by RT-PCR

As a primer set specific to *Treponema* bacteria, total treponemas primers (Forward Primer: TTACGTGCCAGCAGCCGCGGTAAC (SEQ ID NO: 1), Reverse Primer: GTCRYMGGCAGTTCCGCCWGAGTC (SEQ ID NO: 2)) described in the reference "Asai, Y., et al., Detection and quantification of oral treponemes in subgingival plaque by real-time PCR. J Clin Microbiol, 2002. 40(9): 3334-40." were synthesized and used for detection. Specifically, reverse transcription was performed using the RNAs obtained from the tonsils of the IgA nephropathy patients and of the chronic tonsillitis patients set forth in Example 1, and PCR was performed using each of the resulting cDNAs as a template and the above-mentioned primer set (SEQ ID NOs: 1 and 2). PCR conditions are as follows: after denaturation at 95° C. for 5 minutes, 25 cycles of 95° C. for 30 seconds, 69.5° C. for 60 seconds and 72° C. for 1 minute were performed. After the reaction mixture was subjected to electrophoresis on an agarose gel, the gel was stained with SYBR Green I (Lonza, Rockland, Me., USA) and then imaged with the gel imaging system GelDoc XR (Bio-Rad laboratories).

Figure 2:
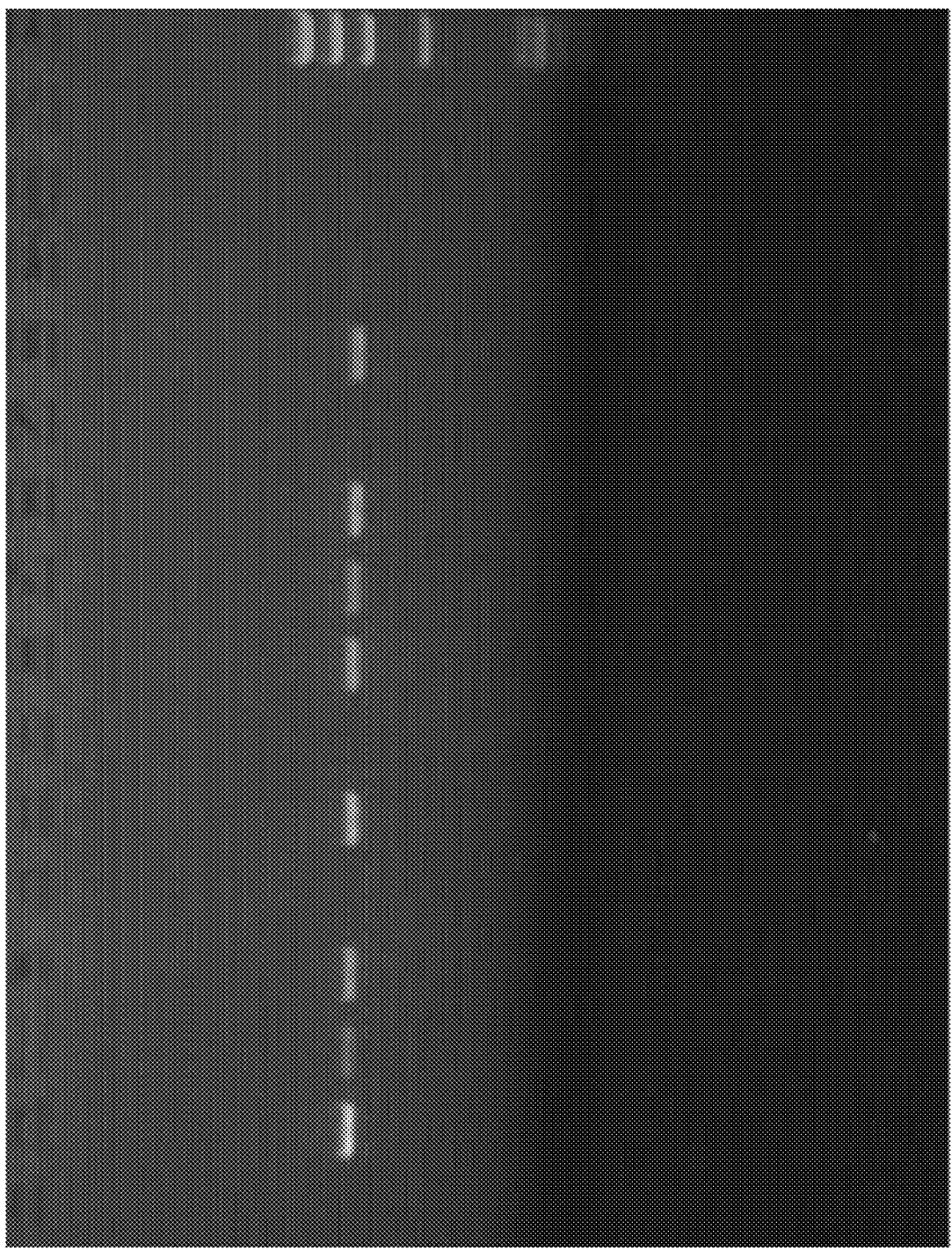
FIG. 2 is an electrophoretic pattern showing RT-PCR detection of *Treponema* bacteria present in excised tonsils.

The result of the electrophoresis is shown in FIG. 2. It was confirmed that the band at 657 bp was observed in the samples shown as *Treponema* positive in the DGGE of Example 1 while the band was not observed in the negative samples. This result showed that *Treponema* bacteria present in the tonsil are detectable by RT-PCR.

Example 3

Detection of *Campylobacter rectus* in Excised Tonsil by RT-PCR

As a primer set specific to *Campylobacter rectus*, primers (Forward Primer: TTTCGGAGCGTAAACTCCTTTTC (SEQ ID NO: 9), Reverse Primer: TTTCTGCAAGCAGACACTCTT (SEQ ID NO: 10)) described in the reference "Hayashi, F., et al., Subgingival distribution of *Campylobacter rectus* and *Tannerella forsythensis* in healthy children with primary dentition. Archives of Oral Biology, 2006. 51: 10-14." were synthesized and used for detection. The procedures for the detection were the same as in Example 2 except for using different primers.

Figure 3:
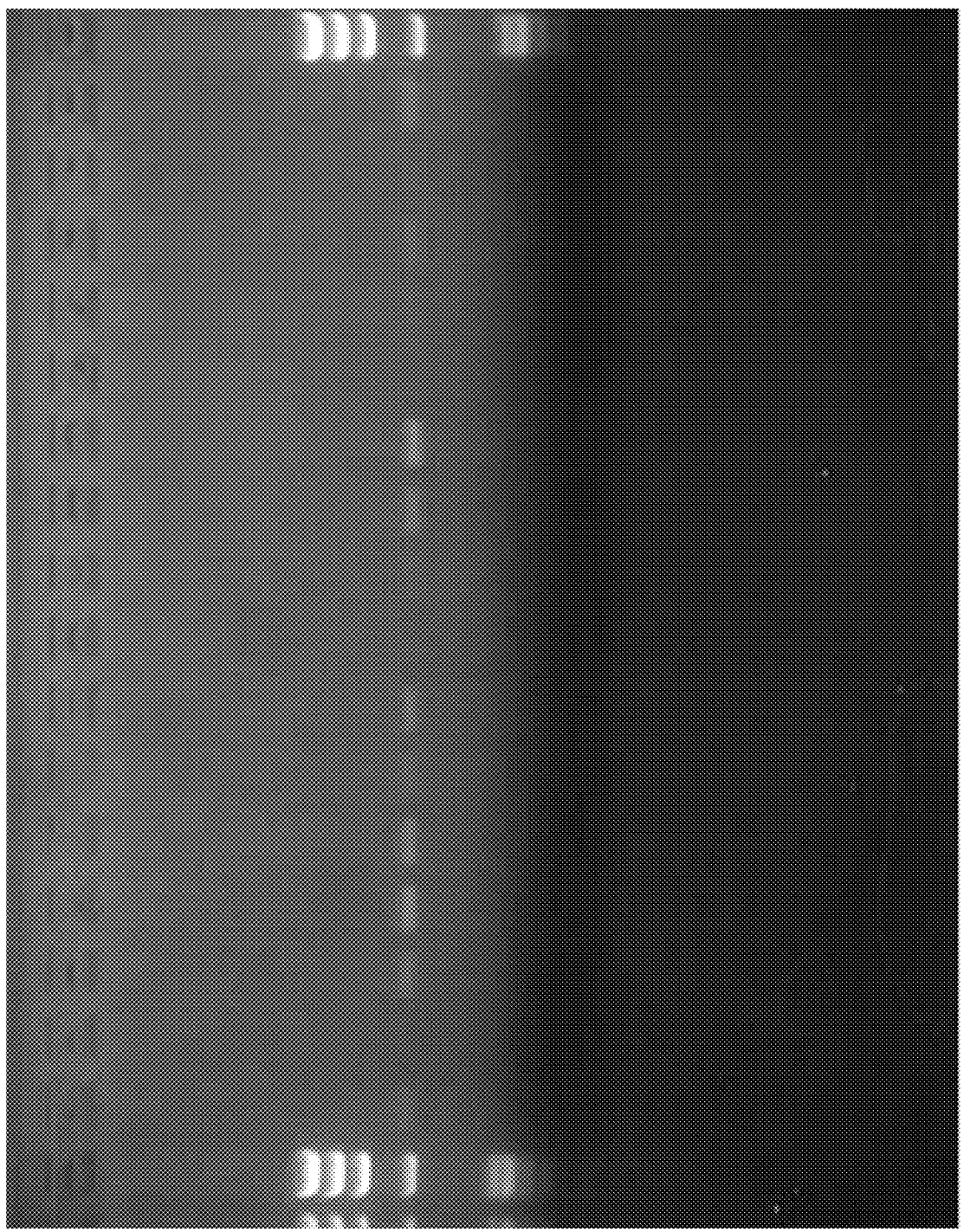
FIG. 3 is an electrophoretic pattern showing RT-PCR detection of *Campylobacter rectus* present in excised tonsils.

The result of the electrophoresis is shown in FIG. 3. It was confirmed that the band at 598 bp was observed in the samples shown as *Campylobacter rectus* positive in the DGGE of Example 1 while the band was not observed in the negative samples. This result showed that *Campylobacter rectus* present in the tonsil is detectable by RT-PCR.

Example 4

Detection of *Treponema* Bacteria and *Campylobacter rectus* in Tonsil Swab by RT-PCR Under direct vision, a clean swab was rubbed against the tonsil of the IgA nephropathy patient for collection of tonsil swab. RNA was extracted from the obtained tonsil swab by use of Trizol (Invitrogen) and then subjected to reverse transcription. The resulting cDNA was used as a template, and using the above-mentioned primer set specific to *Treponema* bacteria (SEQ ID NOs: 1 and 2) or primer set specific to *Campylobacter rectus* (SEQ ID NOs: 9 and 10), PCR was performed in the same conditions as in Example 2.

The results showed that, even in the case where tonsil swab is used as a sample, *Treponema* bacteria and *Campylobacter rectus* are detectable by RT-PCR. Accordingly, it became clear that patients' burden at the time of sample collection can be significantly reduced.

Example 5

Correlation Between Tonsil Bacteria and Therapeutic Effect

The presence of correlation between the kind of bacteria detected in the tonsil and the effectiveness of tonsillectomy plus steroid pulse therapy was examined.

The protocol of tonsillectomy plus steroid pulse therapy is as follows. That is, steroid pulse treatment (intravenous administration of 500 mg of steroid) was provided for 3 days from 1 week to 10 days after tonsillectomy, and then 1 mg per kg of body weight of Predonine (steroid) (up to 60 mg) was administered orally for 10 to 14 days. Afterwards, the steroid pulse treatment was provided again for 3 days, and then 30 mg of steroid was administered orally. At this point, patients were discharged from hospital. After that, the oral dosage was tapered by 5 mg during follow-up visits and the oral administration was discontinued in half a year to 1 year.

About 3 times/week during hospitalization (till the completion of the second steroid pulse treatment) and once in 1 to 2 months after discharge, urinalysis was performed to check whether the test results became negative for proteinuria and hematuria.

Figure 4:
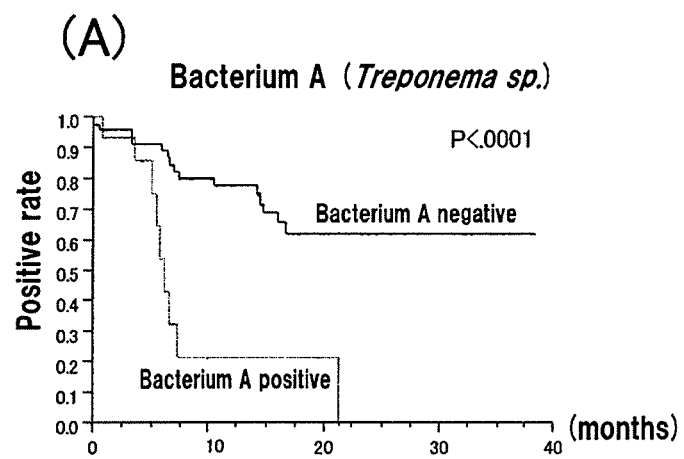
FIG. 4(A) is a graph showing the therapeutic effect of tonsillectomy plus steroid pulse therapy in the presence or absence of *Treponema* bacteria in the tonsil.
FIG. 4(B) is a graph showing the therapeutic effect of tonsillectomy plus steroid pulse therapy in the presence or absence of *Haemophilus* bacteria in the tonsil.
FIG. 4(C) is a graph showing the therapeutic effect of tonsillectomy plus steroid pulse therapy in the presence or absence of *Campylobacter* bacteria in the tonsil.
Figure 4B:
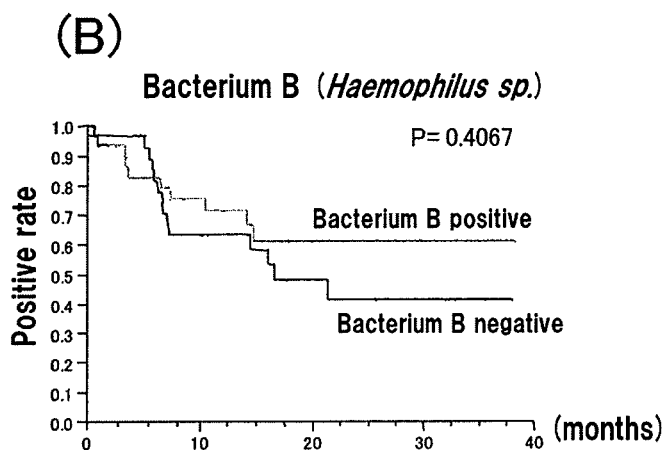
Figure 4C:
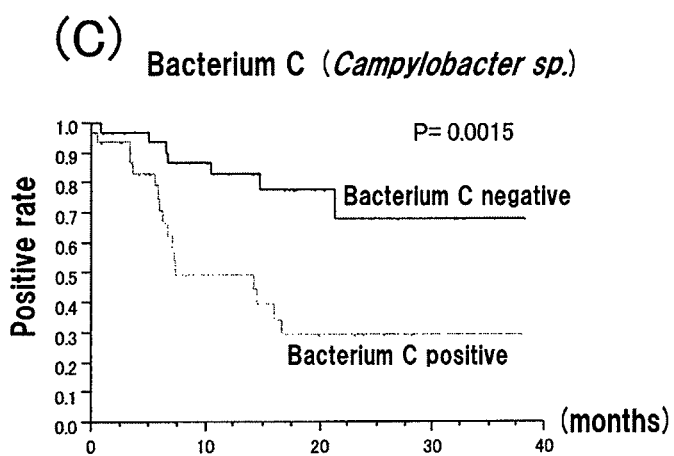

The results were shown in FIGS. 4(A) to (C). (A), (B) and (C) show the results on *Treponema* bacteria, *Haemophilus* bacteria and *Campylobacter* bacteria, respectively. The vertical axis indicates the positive rate. When subjects were positive for at least one of proteinuria and hematuria, they were determined as positive, and calculation of the positive rate was based on this determination. Survival analysis was also performed according to the Kaplan-Meier method by use of the statistical analysis software JMP.

As is clear from FIG. 4(A), within 2 years after the tonsillectomy plus steroid pulse therapy was provided to the IgA nephropathy patients who had been positive in detection of *Treponema* bacteria in the tonsil, all the patients became negative (achieved complete remission) for both of proteinuria and hematuria. On the other hand, less than 40% of the patients who had been negative in detection of *Treponema* bacteria in the tonsil achieved complete remission.

As is clear from FIG. 4(B), the presence of *Haemophilus* bacteria in the tonsil did not affect the effectiveness of the tonsillectomy plus steroid pulse therapy.

As is clear from FIG. 4(C), at 40 months after the tonsillectomy plus steroid pulse therapy was provided to the IgA nephropathy patients who had been positive in detection of *Campylobacter* bacteria in the tonsil, about 70% of the patients achieved complete remission (became negative for both of proteinuria and hematuria). On the other hand, less than 30% of the patients who had been negative in detection of *Campylobacter* bacteria in the tonsil achieved complete remission.

These results showed that it is greatly effective to provide tonsillectomy plus steroid pulse therapy to IgA nephropathy patients who are positive for *Treponema* bacteria or *Campylobacter* bacteria in the tonsil.

From the above results, in the case where *Treponema* bacteria and/or *Campylobacter* bacteria are detected in the tonsil of a subject who is positive for proteinuria and hematuria based on urinalysis, the subject can be diagnosed with highly probable IgA nephropathy. Further, in the case where *Treponema* bacteria and/or *Campylobacter* bacteria are detected in the tonsil of an IgA nephropathy patient, it is possible to presume before tonsillectomy that tonsillectomy plus steroid pulse therapy is extremely effective for the IgA nephropathy patient.

The present invention is not limited to the aforementioned embodiments and examples, and various modifications can be made within the scope of the appended claims. Other embodiments obtainable by suitably combining technical means disclosed in different embodiments of the present invention are also included in the technical scope of the present invention. All the academic publications and patent literature cited in this description are incorporated herein by reference.

The invention claimed is:

1. A method for detecting presumed IgA nephropathy in a subject, comprising
assaying a sample from a tonsil of the subject by polymerase chain reaction using primer pairs selected from the group consisting of SEQ ID NO: 1 and SEQ ID NO: 2, SEQ ID NO: 3 and SEQ ID NO: 4, SEQ ID NO: 5 and SEQ ID NO: 6, and SEQ ID NO: 7 and SEQ ID NO: 8, to detect a nucleic acid specific to *Treponema* bacteria, wherein detection of a nucleic acid specific to *Treponema* bacteria indicates that the subject has presumed IgA nephropathy.

2. The method according to claim 1, wherein the *Treponema* bacteria is one or more selected from the group consisting of *Treponema denticola, Treponema vincentii, Treponema medium, Treponema socranskii, Treponema phagedenis, Treponema pectinovorum, Treponema amylovorum, Treponema maltophilum, Treponema bryantii, Treponema pallidum, Treponema saccharophilum* and *Treponema succinifaciens*.

3. The method according to claim 1, wherein the subject has a positive result on a urinary protein test and/or a urinary occult blood test.

4. A method for determining if tonsillectomy will be effective for treatment of an IgA nephropathy patient, comprising
assaying a sample from a tonsil of the patient by polymerase chain reaction using primer pairs selected from the group consisting of SEQ ID NO: 1 and SEQ ID NO: 2, SEQ ID NO: 3 and SEQ ID NO: 4, SEQ ID NO: 5 and SEQ ID NO: 6, and SEQ ID NO: 7 and SEQ ID NO: 8, to detect a nucleic acid specific to Treponema bacteria, wherein detection of a nucleic acid specific to Treponema bacteria indicates that tonsillectomy will be an effective therapy for the patient.

5. The method according to claim 4, wherein the Treponema bacteria is one or more selected from the group consisting of *Treponema denticola, Treponema vincentii, Treponema medium, Treponema socranskii, Treponema phagedenis, Treponema pectinovorum, Treponema amylovorum, Treponema maltophilum, Treponema bryantii, Treponema pallidum, Treponema saccharophilum* and *Treponema succinifaciens*.

6. A method for determining if tonsillectomy and steroid pulse therapy will be effective for treatment of an IgA nephropathy patient, comprising
assaying a sample from a tonsil of the patient by polymerase chain reaction using primer pairs selected from the group consisting of SEQ ID NO: 1 and SEQ ID NO: 2, SEQ ID NO: 3 and SEQ ID NO: 4, SEQ ID NO: 5 and SEQ ID NO: 6, and SEQ ID NO: 7 and SEQ ID NO: 8, to detect a nucleic acid specific to *Treponema* bacteria, wherein detection of a nucleic acid specific to *Treponema* bacteria indicates that tonsillectomy and steroid pulse therapy will be an effective therapy for the patient.

7. The method according to claim 6, wherein the *Treponema* bacteria is one or more selected from the group consisting of *Treponema denticola, Treponema vincentii, Treponema medium, Treponema socranskii, Treponema phagedenis, Treponema pectinovorum, Treponema amylovorum, Treponema maltophilum, Treponema bryantii, Treponema pallidum, Treponema saccharophilum* and *Treponema succinifaciens*.

8. A method for detecting presumed IgA nephropathy in a subject, comprising assaying a sample from a tonsil of the subject by polymerase chain reaction using primer pairs selected from the group consisting of:
SEQ ID NO: 9 and SEQ ID NO: 10, SEQ ID NO: 11 and SEQ ID NO: 12, SEQ ID NO: 13 and SEQ ID NO: 14, SEQ ID NO: 15 and SEQ ID NO: 16, SEQ ID NO: 17 and SEQ ID NO: 18, SEQ ID NO: 19 and SEQ ID NO: 20, SEQ ID NO: 21 and SEQ ID NO: 22, SEQ ID NO: 23 and SEQ ID NO: 24, SEQ ID NO: 25 and SEQ ID NO: 26, SEQ ID NO: 27 and SEQ ID NO: 28, SEQ ID NO: 29 and SEQ ID NO: 30, SEQ ID NO: 31 and SEQ ID NO: 32, and SEQ ID NO: 33 and SEQ ID NO: 34,
to detect a nucleic acid specific to *Campylobacter* bacteria, wherein detection of a nucleic acid specific to Campylobacter bacteria selected from the group consisting of *Campylobacter rectus, Campylobacter coli, Campylobacter concisus, Campylobacter curvus, Campylobacter showae, Campylobacter mucosalis, Campylobacter fetus, Campylobacter hyointestinalis, Campylobacter sputorum, Campylobacter helveticus, Campylobacter upsaliensis* and *Campylobacter lari* indicates that the subject has presumed IgA nephropathy.

9. The method according to claim 8, wherein the subject has a positive result on at least one of a urinary protein test and a urinary occult blood test.

10. A method for determining if tonsillectomy will be effective for treatment of an IgA nephropathy patient, comprising assaying a sample from a tonsil of the patient by polymerase chain reaction using primer pairs selected from the group consisting of:
SEQ ID NO: 9 and SEQ ID NO: 10, SEQ ID NO: 11 and SEQ ID NO: 12, SEQ ID NO: 13 and SEQ ID NO: 14, SEQ ID NO: 15 and SEQ ID NO: 16, SEQ ID NO: 17 and SEQ ID NO: 18, SEQ ID NO: 19 and SEQ ID NO: 20, SEQ ID NO: 21 and SEQ ID NO: 22, SEQ ID NO: 23 and SEQ ID NO: 24, SEQ ID NO: 25 and SEQ ID NO: 26, SEQ ID NO: 27 and SEQ ID NO: 28, SEQ ID NO: 29 and SEQ ID NO: 30, SEQ ID NO: 31 and SEQ ID NO: 32, and SEQ ID NO: 33 and SEQ ID NO: 34,
to detect a nucleic acid specific to *Campylobacter* bacteria, wherein detection of a nucleic acid specific to *Campylobacter* bacteria selected from the group consisting of *Campylobacter rectus*, *Campylobacter coli*, *Campylobacter concisus*, *Campylobacter curvus*, *Campylobacter showae*, *Campylobacter mucosalis*, *Campylobacter fetus*, *Campylobacter hyointestinalis*, *Campylobacter sputorum*, *Campylobacter helveticus*, *Campylobacter upsaliensis* and *Campylobacter lari* indicates that tonsillectomy will be an effective therapy for the patient.

11. A method for determining if tonsillectomy and steroid pulse therapy will be effective for treatment of an IgA nephropathy patient, comprising
assaying a sample from a tonsil of the subject by polymerase chain reaction using primer pairs selected from the group consisting of:
SEQ ID NO: 9 and SEQ ID NO: 10, SEQ ID NO: 11 and SEQ ID NO: 12, SEQ ID NO: 13 and SEQ ID NO: 14, SEQ ID NO: 15 and SEQ ID NO: 16, SEQ ID NO: 17 and SEQ ID NO: 18, SEQ ID NO: 19 and SEQ ID NO: 20, SEQ ID NO: 21 and SEQ ID NO: 22, SEQ ID NO: 23 and SEQ ID NO: 24, SEQ ID NO: 25 and SEQ ID NO: 26, SEQ ID NO: 27 and SEQ ID NO: 28, SEQ ID NO: 29 and SEQ ID NO: 30, SEQ ID NO: 31 and SEQ ID NO: 32, and SEQ ID NO: 33 and SEQ ID NO: 34,
to detect a nucleic acid specific to *Campylobacter* bacteria, wherein detection of a nucleic acid specific to *Campylobacter* bacteria selected from the group consisting of *Campylobacter rectus*, *Campylobacter coli*, *Campylobacter concisus*, *Campylobacter curvus*, *Campylobacter showae*, *Campylobacter mucosalis*, *Campylobacter fetus*, *Campylobacter hyointestinalis*, *Campylobacter sputorum*, *Campylobacter helveticus*, *Campylobacter upsaliensis* and *Campylobacter lari* indicates that tonsillectomy and steroid pulse therapy will be an effective therapy for the patient.

12. A method for detecting presumed IgA nephropathy in a subject, comprising
assaying a sample from a tonsil of the subject by polymerase chain reaction using primer pairs selected from the group consisting of SEQ ID NO: 1 and SEQ ID NO: 2, SEQ ID NO: 3 and SEQ ID NO: 4, SEQ ID NO: 5 and SEQ ID NO: 6, and SEQ ID NO: 7 and SEQ ID NO: 8,
to detect a nucleic acid specific to *Treponema* bacteria, and assaying the sample by polymerase chain reaction using primer pairs selected from the group consisting of:
SEQ ID NO: 9 and SEQ ID NO: 10, SEQ ID NO: 11 and SEQ ID NO: 12, SEQ ID NO: 13 and SEQ ID NO: 14, SEQ ID NO: 15 and SEQ ID NO: 16, SEQ ID NO: 17 and SEQ ID NO: 18, SEQ ID NO: 19 and SEQ ID NO: 20, SEQ ID NO: 21 and SEQ ID NO: 22, SEQ ID NO: 23 and SEQ ID NO: 24, SEQ ID NO: 25 and SEQ ID NO: 26, SEQ ID NO: 27 and SEQ ID NO: 28, SEQ ID NO: 29 and SEQ ID NO: 30, SEQ ID NO: 31 and SEQ ID NO: 32, and SEQ ID NO: 33 and SEQ ID NO: 34,
to detect a nucleic acid specific to *Campylobacter* bacteria, wherein detection of a nucleic acid specific to *Treponema* bacteria and detection of a nucleic acid specific to *Campylobacter* bacteria selected from the group consisting of *Campylobacter rectus*, *Campylobacter coli*, *Campylobacter concisus*, *Campylobacter curvus*, *Campylobacter showae*, *Campylobacter mucosalis*, *Campylobacter fetus*, *Campylobacter hyointestinalis*, *Campylobacter sputorum*, *Campylobacter helveticus*, *Campylobacter upsaliensis* and *Campylobacter lari* indicates that the subject has presumed IgA nephropathy.

13. The method according to claim 12, wherein the *Treponema* bacteria is one or more selected from the group consisting of *Treponema denticola*, *Treponema vincentii*, *Treponema medium*, *Treponema socranskii*, *Treponema phagedenis*, *Treponema pectinovorum*, *Treponema amylovorum*, *Treponema maltophilum*, *Treponema bryantii*, *Treponema pallidum*, *Treponema saccharophilum* and *Treponema succinifaciens*.

14. The method according to claim 12, wherein the subject has a positive result on at least one of a urinary protein test and a urinary occult blood test.

15. A method for determining if tonsillectomy will be effective for treatment of an IgA nephropathy patient, comprising
assaying a sample from a tonsil of the patient by polymerase chain reaction using primer pairs selected from the group consisting of SEQ ID NO: 1 and SEQ ID NO: 2, SEQ ID NO: 3 and SEQ ID NO: 4, SEQ ID NO: 5 and SEQ ID NO: 6, and SEQ ID NO: 7 and SEQ ID NO: 8,
to detect a nucleic acid specific to *Treponema* bacteria, and assaying the sample by polymerase chain reaction using primer pairs selected from the group consisting of:
SEQ ID NO: 9 and SEQ ID NO: 10, SEQ ID NO: 11 and SEQ ID NO: 12, SEQ ID NO: 13 and SEQ ID NO: 14, SEQ ID NO: 15 and SEQ ID NO: 16, SEQ ID NO: 17 and SEQ ID NO: 18, SEQ ID NO: 19 and SEQ ID NO: 20, SEQ ID NO: 21 and SEQ ID NO: 22, SEQ ID NO: 23 and SEQ ID NO: 24, SEQ ID NO: 25 and SEQ ID NO: 26, SEQ ID NO: 27 and SEQ ID NO: 28, SEQ ID NO: 29 and SEQ ID NO: 30, SEQ ID NO: 31 and SEQ ID NO: 32, and SEQ ID NO: 33 and SEQ ID NO: 34,
to detect a nucleic acid specific to *Campylobacter* bacteria, wherein detection of a nucleic acid specific to *Treponema* bacteria and detection of a nucleic acid specific to *Campylobacter* bacteria selected from the group consisting of *Campylobacter rectus*, *Campylobacter coli*, *Campylobacter concisus*, *Campylobacter curvus*, *Campylobacter showae*, *Campylobacter mucosalis*, *Campylobacter fetus*, *Campylobacter hyointestinalis*, *Campylobacter sputorum*, *Campylobacter helveticus*, *Campylobacter upsaliensis* and *Campylobacter lari* indicates that tonsillectomy will be an effective therapy for the patient.

16. The method according to claim 15, wherein the *Treponema* bacteria is one or more selected from the group consisting of *Treponema denticola*, *Treponema vincentii*, *Treponema medium*, *Treponema socranskii*, *Treponema phagedenis*, *Treponema pectinovorum*, *Treponema amylovorum*, *Treponema maltophilum*, *Treponema bryantii*, *Treponema pallidum*, *Treponema saccharophilum* and *Treponema succinifaciens*.

17. A method for determining if tonsillectomy and steroid pulse therapy will be effective for treatment of an IgA nephropathy patient, comprising
assaying a sample from a tonsil of the subject by polymerase chain reaction using primer pairs selected from the group consisting of SEQ ID NO: 1 and SEQ ID NO: 2, SEQ ID NO: 3 and SEQ ID NO: 4, SEQ ID NO: 5 and SEQ ID NO: 6, and SEQ ID NO: 7 and SEQ ID NO: 8, to detect a nucleic acid specific to Treponema bacteria, and assaying the sample by polymerase chain reaction using primer pairs selected from the group consisting of:

SEQ ID NO: 9 and SEQ ID NO: 10, SEQ ID NO: 11 and SEQ ID NO: 12, SEQ ID NO: 13 and SEQ ID NO: 14, SEQ ID NO: 15 and SEQ ID NO: 16, SEQ ID NO: 17 and SEQ ID NO: 18, SEQ ID NO: 19 and SEQ ID NO: 20, SEQ ID NO: 21 and SEQ ID NO: 22, SEQ ID NO: 23 and SEQ ID NO: 24, SEQ ID NO: 25 and SEQ ID NO: 26, SEQ ID NO: 27 and SEQ ID NO: 28, SEQ ID NO: 29 and SEQ ID NO: 30, SEQ ID NO: 31 and SEQ ID NO: 32, and SEQ ID NO: 33 and SEQ ID NO: 34, to detect a nucleic acid specific to *Campylobacter* bacteria, wherein detection of a nucleic acid specific to *Treponema* bacteria and detection of a nucleic acid specific to *Campylobacter* bacteria selected from the group consisting of *Campylobacter rectus, Campylobacter coli, Campylobacter concisus, Campylobacter curvus, Campylobacter showae, Campylobacter mucosalis, Campylobacter fetus, Campylobacter hyointestinalis, Campylobacter sputorum, Campylobacter helveticus, Campylobacter upsaliensis* and *Campylobacter lari* indicates that tonsillectomy and steroid pulse therapy will be an effective therapy for the patient.

18. The method according to claim 17, wherein the *Treponema* bacteria is one or more selected from the group consisting of *Treponema denticola, Treponema vincentii, Treponema medium, Treponema socranskii, Treponema phagedenis, Treponema pectinovorum, Treponema amylovorum, Treponema maltophilum, Treponema bryantii, Treponema pallidum, Treponema saccharophilum* and *Treponema succinifaciens*.

* * * * *

SEQUENCE LISTING

```
<160> NUMBER OF SEQ ID NOS: 36

<210> SEQ ID NO 1
<211> LENGTH: 24
<212> TYPE: DNA
<213> ORGANISM: Artificial
<220> FEATURE:
<223> OTHER INFORMATION: Treponema sp. specific PCR primer

<400> SEQUENCE: 1
ttacgtgcca gcagccgcgg taac                                          24

<210> SEQ ID NO 2
<211> LENGTH: 24
```

```
<212> TYPE: DNA
<213> ORGANISM: Artificial
<220> FEATURE:
<223> OTHER INFORMATION: Treponema sp. specific PCR primer

<400> SEQUENCE: 2
gtcrymggca gttccgccwg agtc                                          24

<210> SEQ ID NO 3
<211> LENGTH: 25
<212> TYPE: DNA
<213> ORGANISM: Artificial
<220> FEATURE:
<223> OTHER INFORMATION: Treponema denticola specific PCR primer

<400> SEQUENCE: 3
taataccgaa tgtgctcatt tacat                                         25

<210> SEQ ID NO 4
<211> LENGTH: 27
<212> TYPE: DNA
<213> ORGANISM: Artificial
<220> FEATURE:
<223> OTHER INFORMATION: Treponema denticola specific PCR primer

<400> SEQUENCE: 4
ctgccatatc tctatgtcat tgctctt                                       27

<210> SEQ ID NO 5
<211> LENGTH: 20
<212> TYPE: DNA
<213> ORGANISM: Artificial
<220> FEATURE:
<223> OTHER INFORMATION: Treponema vincentii specific PCR primer

<400> SEQUENCE: 5
gtctcaatgg ttcataagaa                                               20

<210> SEQ ID NO 6
<211> LENGTH: 20
<212> TYPE: DNA
<213> ORGANISM: Artificial
<220> FEATURE:
<223> OTHER INFORMATION: Treponema vincentii specific PCR primer

<400> SEQUENCE: 6
caagccttat ctctaagact                                               20

<210> SEQ ID NO 7
<211> LENGTH: 20
<212> TYPE: DNA
<213> ORGANISM: Artificial
<220> FEATURE:
<223> OTHER INFORMATION: Treponema medium specific PCR primer

<400> SEQUENCE: 7
cactcagtgc ttcataaggg                                               20

<210> SEQ ID NO 8
<211> LENGTH: 20
<212> TYPE: DNA
<213> ORGANISM: Artificial
<220> FEATURE:
<223> OTHER INFORMATION: Treponema medium specific PCR primer

<400> SEQUENCE: 8
ccggccttat ctctaagacc                                               20
```

<210> SEQ ID NO 9
<211> LENGTH: 23
<212> TYPE: DNA
<213> ORGANISM: Artificial
<220> FEATURE:
<223> OTHER INFORMATION: Campylobacter rectus specific PCR primer

<400> SEQUENCE: 9
tttcggagcg taaactcctt ttc                                    23

<210> SEQ ID NO 10
<211> LENGTH: 21
<212> TYPE: DNA
<213> ORGANISM: Artificial
<220> FEATURE:
<223> OTHER INFORMATION: Campylobacter rectus specific PCR primer

<400> SEQUENCE: 10
tttctgcaag cagacactct t                                      21

<210> SEQ ID NO 11
<211> LENGTH: 27
<212> TYPE: DNA
<213> ORGANISM: Artificial
<220> FEATURE:
<223> OTHER INFORMATION: Campylobacter jejuni specific PCR primer

<400> SEQUENCE: 11
agaatgggtt taactcgtgt gataagt                                27

<210> SEQ ID NO 12
<211> LENGTH: 23
<212> TYPE: DNA
<213> ORGANISM: Artificial
<220> FEATURE:
<223> OTHER INFORMATION: Campylobacter jejuni specific PCR primer

<400> SEQUENCE: 12
taccacgcaa aggcagtata gct                                    23

<210> SEQ ID NO 13
<211> LENGTH: 28
<212> TYPE: DNA
<213> ORGANISM: Artificial
<220> FEATURE:
<223> OTHER INFORMATION: Campylobacter coli specific PCR primer

<400> SEQUENCE: 13
aaatgctagt gctagggaaa aagactct                               28

<210> SEQ ID NO 14
<211> LENGTH: 29
<212> TYPE: DNA
<213> ORGANISM: Artificial
<220> FEATURE:
<223> OTHER INFORMATION: Campylobacter coli specific PCR primer

<400> SEQUENCE: 14
tgaggttcag gcacttttac acttactac                              29

<210> SEQ ID NO 15
<211> LENGTH: 25
<212> TYPE: DNA
<213> ORGANISM: Artificial
<220> FEATURE:
<223> OTHER INFORMATION: Campylobacter concisus specific PCR primer

<400> SEQUENCE: 15
agcgggccta acaagagtta ttaca                                              25

<210> SEQ ID NO 16
<211> LENGTH: 25
<212> TYPE: DNA
<213> ORGANISM: Artificial
<220> FEATURE:
<223> OTHER INFORMATION: Campylobacter concisus specific PCR primer

<400> SEQUENCE: 16
tgtaagcacg tcaaaaacca tcttt                                              25

<210> SEQ ID NO 17
<211> LENGTH: 25
<212> TYPE: DNA
<213> ORGANISM: Artificial
<220> FEATURE:
<223> OTHER INFORMATION: Campylobacter curvus specific PCR primer

<400> SEQUENCE: 17
ctgccaaagt aaggacgcaa gtata                                              25

<210> SEQ ID NO 18
<211> LENGTH: 21
<212> TYPE: DNA
<213> ORGANISM: Artificial
<220> FEATURE:
<223> OTHER INFORMATION: Campylobacter curvus specific PCR primer

<400> SEQUENCE: 18
ggcaagatcg cctgaaatac g                                                  21

<210> SEQ ID NO 19
<211> LENGTH: 23
<212> TYPE: DNA
<213> ORGANISM: Artificial
<220> FEATURE:
<223> OTHER INFORMATION: Campylobacter showae specific PCR primer

<400> SEQUENCE: 19
agggtttaag cataggaacg ctg                                                23

<210> SEQ ID NO 20
<211> LENGTH: 23
<212> TYPE: DNA
<213> ORGANISM: Artificial
<220> FEATURE:
<223> OTHER INFORMATION: Campylobacter showae specific PCR primer

<400> SEQUENCE: 20
caccagataa agctcgctga tcg                                                23

<210> SEQ ID NO 21
<211> LENGTH: 22
<212> TYPE: DNA
<213> ORGANISM: Artificial
<220> FEATURE:
<223> OTHER INFORMATION: Campylobacter mucosalis specific PCR primer

<400> SEQUENCE: 21
tgcgattatg aacaaggccc ta                                                 22

<210> SEQ ID NO 22
<211> LENGTH: 20

```
<212> TYPE: DNA
<213> ORGANISM: Artificial
<220> FEATURE:
<223> OTHER INFORMATION: Campylobacter mucosalis specific PCR primer

<400> SEQUENCE: 22
tcgcttgaaa cacacggtca                                              20

<210> SEQ ID NO 23
<211> LENGTH: 27
<212> TYPE: DNA
<213> ORGANISM: Artificial
<220> FEATURE:
<223> OTHER INFORMATION: Campylobacter fetus specific PCR primer

<400> SEQUENCE: 23
agagctgggc ttacaagagc tattaca                                      27

<210> SEQ ID NO 24
<211> LENGTH: 25
<212> TYPE: DNA
<213> ORGANISM: Artificial
<220> FEATURE:
<223> OTHER INFORMATION: Campylobacter fetus specific PCR primer

<400> SEQUENCE: 24
ggtaaaatcg cttgaaacgc tctat                                        25

<210> SEQ ID NO 25
<211> LENGTH: 28
<212> TYPE: DNA
<213> ORGANISM: Artificial
<220> FEATURE:
<223> OTHER INFORMATION: Campylobacter hyointestinalis specific PCR
      primer

<400> SEQUENCE: 25
cggtcaaaag atgactttg aagtactt                                      28

<210> SEQ ID NO 26
<211> LENGTH: 18
<212> TYPE: DNA
<213> ORGANISM: Artificial
<220> FEATURE:
<223> OTHER INFORMATION: Campylobacter hyointestinalis specific PCR
      primer

<400> SEQUENCE: 26
gcttccctgc cacgagct                                                18

<210> SEQ ID NO 27
<211> LENGTH: 25
<212> TYPE: DNA
<213> ORGANISM: Artificial
<220> FEATURE:
<223> OTHER INFORMATION: Campylobacter sputorum specific PCR primer

<400> SEQUENCE: 27
agctttactt gctgcaagag gaaga                                        25

<210> SEQ ID NO 28
<211> LENGTH: 24
<212> TYPE: DNA
<213> ORGANISM: Artificial
<220> FEATURE:
<223> OTHER INFORMATION: Campylobacter sputorum specific PCR primer

<400> SEQUENCE: 28
```
aggaagcgtt ccaacagaaa agtt                                           24

<210> SEQ ID NO 29
<211> LENGTH: 25
<212> TYPE: DNA
<213> ORGANISM: Artificial
<220> FEATURE:
<223> OTHER INFORMATION: Campylobacter helveticus specific PCR primer

<400> SEQUENCE: 29
caataacata cgcacaccag atgga                                          25

<210> SEQ ID NO 30
<211> LENGTH: 24
<212> TYPE: DNA
<213> ORGANISM: Artificial
<220> FEATURE:
<223> OTHER INFORMATION: Campylobacter helveticus specific PCR primer

<400> SEQUENCE: 30
caggcacttt aacgctcact atgg                                           24

<210> SEQ ID NO 31
<211> LENGTH: 28
<212> TYPE: DNA
<213> ORGANISM: Artificial
<220> FEATURE:
<223> OTHER INFORMATION: Campylobacter upsaliensis specific PCR primer

<400> SEQUENCE: 31
gcttacgcgt gtaattacaa actatgtc                                       28

<210> SEQ ID NO 32
<211> LENGTH: 22
<212> TYPE: DNA
<213> ORGANISM: Artificial
<220> FEATURE:
<223> OTHER INFORMATION: Campylobacter upsaliensis specific PCR primer

<400> SEQUENCE: 32
aattgcctta gcctcgatag gg                                             22

<210> SEQ ID NO 33
<211> LENGTH: 30
<212> TYPE: DNA
<213> ORGANISM: Artificial
<220> FEATURE:
<223> OTHER INFORMATION: Campylobacter lari specific PCR primer

<400> SEQUENCE: 33
ctatgttcgt cctatagttt ctaaggcttc                                     30

<210> SEQ ID NO 34
<211> LENGTH: 27
<212> TYPE: DNA
<213> ORGANISM: Artificial
<220> FEATURE:
<223> OTHER INFORMATION: Campylobacter lari specific PCR primer

<400> SEQUENCE: 34
ccagcactat caccctcaac taaataa                                        27

<210> SEQ ID NO 35
<211> LENGTH: 62
<212> TYPE: DNA
<213> ORGANISM: Artificial

-continued

```
<220> FEATURE:
<223> OTHER INFORMATION: bacteria specific PCR primer

<400> SEQUENCE: 35
cgcccgccgc gccccgcgcc cggcccgccg ccccccgcccc gcacaagcgg tggagcatgt      60
gg                                                                      62

<210> SEQ ID NO 36
<211> LENGTH: 20
<212> TYPE: DNA
<213> ORGANISM: Artificial
<220> FEATURE:
<223> OTHER INFORMATION: bacteria specific PCR primer

<400> SEQUENCE: 36
gcccgggaac gtattcaccg                                                   20
```